United States Patent [19]

Paspa et al.

[11] Patent Number: 5,662,692

[45] Date of Patent: Sep. 2, 1997

[54] CARDIAC DEFIBRILLATOR HAVING SELECTABLE POLARITY CASE

[75] Inventors: Paul M. Paspa, Santa Clara; M. Elizabeth Bush, Fremont, both of Calif.

[73] Assignee: Pacesetter, Inc., Sunnyvale, Calif.

[21] Appl. No.: 463,527

[22] Filed: Jun. 5, 1995

Related U.S. Application Data

[63] Continuation-in-part of Ser. No. 353,422, Dec. 9, 1994, Pat. No. 5,534,019.

[51] Int. Cl.⁶ ............................................. A61N 1/375
[52] U.S. Cl. ............................................. 607/37
[58] Field of Search ............................. 607/2, 4, 5, 9, 607/36–38, 119, 148

[56] References Cited

U.S. PATENT DOCUMENTS

| | | |
|---|---|---|
| 4,301,805 | 11/1981 | Peers-Trevarton et al. . |
| 4,628,934 | 12/1986 | Pohndorf et al. ............ 128/419 |
| 4,727,877 | 3/1988 | Kallok . |
| 4,907,592 | 3/1990 | Harper . |
| 4,922,927 | 5/1990 | Fine et al. . |
| 5,129,394 | 7/1992 | Mehra . |
| 5,133,353 | 7/1992 | Hauser . |
| 5,220,929 | 6/1993 | Marquit ............ 128/898 |
| 5,261,400 | 11/1993 | Bardy ............ 607/5 |
| 5,314,452 | 5/1994 | Hirchberg et al. ............ 607/36 |
| 5,374,279 | 12/1994 | Duffin, Jr. et al. ............ 607/5 |

OTHER PUBLICATIONS

"Low–Energy Endocardial Defibrillation Using an Axiallary or a Pectoral Thoracic Electrode Location", Saksena, et al., Circulation, vol. 88, No. 6, Dec. 1993, pp. 2655–2660.

"Cardiac defibrillators—Connector Assembly for Implantable Defibrillators—Dimensional and Test Requirements", ISO 11318:1993(E, pp. 1–19).

"Cardiac Pacemakers—Part 3: Low–Profile Connectors (IS–1) for Implantable Pacemakers" ISO 5841–3, First Edition, 1992 Dec. 1, pp. i–9.

U.S. Patent Application No. 08/221,811 (Pless, et al), "Pulse Generator with Case that can be Active or Inactive", Ventritex, Inc.

*Primary Examiner*—Jeffrey R. Jastrzab
*Attorney, Agent, or Firm*—Steven M. Mitchell; M. Elizabeth Bush

[57] ABSTRACT

A defibrillator having a housing for enclosing and containing defibrillation pulse generator circuitry, particularly adapted to allow for ease of manufacture and use. At least one surface of the housing is electrically conductive and may be connected to the defibrillation pulse generator circuitry for delivering defibrillating energy to the heart. The defibrillator is provided with two case-activating setscrew blocks isolated from two contacts. By tightening the first setscrew onto its contact, the can is activated and is positive for defibrillation. By tightening the second setscrew instead, the can is activated and is negative for defibrillation. Tightening neither setscrew maintains the inactive status of the can. By using this system, various electrode configurations can be used as required to provide the optimum system for a given patient. The defibrillator generator housing is preferably implanted in the left pectoral region proximate the heart with the conductive surface facing the heart. Other implantable electrodes are discharged against the defibrillator generator housing electrode.

6 Claims, 8 Drawing Sheets

CARDIAC DEFIBRILLATOR HAVING SELECTABLE POLARITY CASE

This is a continuation-in-part of application Ser. No. 08/353,422 filed on Dec. 9, 1994 now U.S. Pat. No. 5,534,019.

FIELD OF THE INVENTION

The present invention relates generally to implantable cardiac stimulation devices, and more specifically to a cardiac defibrillator with a case that is either electrically activated to be positive or negative, or left inactive at the time of implant.

BACKGROUND OF THE INVENTION

There has been substantial work directed towards development of implantable defibrillation systems that avoid the necessity of a thoracotomy. Systems that deliver a defibrillation pulse between one or more endocardial electrodes and an active defibrillator housing are disclosed in U.S. Pat. Nos. 4,727,877 issued to Kallok; 4,922,927 to Fine et al.; 5,129,394 to Mehra; 5,133,353 to Hauser; 5,261,400 to Bardy; and 5,374,279 to Duffin, Jr. et at., all of which are incorporated herein by reference. As used herein, the words "housing", "enclosure", "case", and "can" are synonymous.

If a device is chosen to have an active can and is placed pectorally, it is unlikely that this decision would be changed in the future. If a lead is used subcutaneously and the inactive can implanted abdominally, it is again unlikely that there would be reason to change this, to "activate the can". Even if this decision were reversed, a surgical procedure would likely be required to reposition the can for effective use as an electrode. Therefore, external programmability of this choice of active or inactive can is not needed, allowing the design and manufacture to be less complex.

Thus, while it is desirable to provide a choice of having the device housing function as an active electrode, this choice will almost always be made at the time of device implant, avoiding the added device complexity resulting from having the choice be programmable after implant.

In the invention of Pless et al., U.S. patent application Ser. No. 08/221,811, filed Mar. 31, 1994, now abandoned which is assigned to the assignee of the present invention, a cardiac defibrillator with a case that can be electrically active or inactive is disclosed. A special connector cavity is provided that has one terminal electrically connected to the generator case and a second terminal connected to one pole of the defibrillator output. By plugging in a pin long enough to contact both terminals, the case is activated during a defibrillation shock. No means is disclosed for using a standard connector pin, such as a DF-1 defibrillator connector pin. Because of the desire to be compatible with existing lead connectors without requiring a special adapter, both at initial implant and during a pulse generator replacement, it would be useful if the pulse generator case could be activated while allowing the use of standard lead connectors. The device disclosed in U.S. Pat. No. 5,374,279 to Duffin, Jr. et at. has a similar deficiency in that a special lead connector or plug must be provided to activate the defibrillator case.

In U.S. Pat. No. 4,301,805 to Peers-Trevarton et al., a cardiac pacer connector system is disclosed that is provided with a bridging means for using the pacer case as a reference potential when a unipolar lead is used. When a bipolar pacing/sensing lead is used, the bridging means is not operated, and the pacer case is inactive.

SUMMARY OF THE INVENTION

The present invention is directed toward the provision of a defibrillator that delivers a defibrillation pulse either between at least one transvenous lead electrode and at least a portion of the metal enclosure of the defibrillator, or between at least one transvenous lead electrode and an additional implanted lead electrode located either transvenously, epicardially, or subcutaneously. The decision to use either the pulse generator case as an electrode, or to implant an additional lead, that is, whether the defibrillator can is electrically active or passive, is made by the implanting surgeon at the time of implant.

The defibrillator of the present invention is provided with two metal blocks, each having female setscrew threads and being electrically connected to the pulse generator case. Each setscrew block has a contact, one to the positive high voltage terminal, and one to the negative high voltage terminal. Depending on which setscrew is tightened down onto its corresponding contact, the case may be made positive or negative for defibrillation. By not tightening either setscrew, the defibrillator case is left inactive.

Alternatively, the metal blocks that have female setscrew threads may be provided with the first such block electrically connected to the positive high voltage terminal, and the second such block electrically attached to the negative high voltage terminal of the pulse generator circuitry. Depending on which setscrew is tightened, the case may be made positive or negative during a delivered defibrillation pulse. Tightening neither setscrew maintains the inactive status of the case.

By using the present invention, various electrode configurations can be used as required to provide the optimum system for a given patient without having to bring two defibrillators into the operating room, one having an active can and one having an inactive can, and without requiring any programmability from the manufacturer or programming by the physician. Some patients have a lower defibrillation threshold (DFT) with the subcutaneous (SQ) electrode positive, and some have a lower DFT with the SQ electrode negative. By this invention, both polarities may be easily tested to determine which is best for the patient. This invention also allows the use of standard lead connectors without requiring a special adapter or a lead having a special connector.

It is thus a primary object of this invention to provide an implantable cardiac stimulation system having defibrillation capabilities with a selectable electrode configuration.

It is an additional object of this invention to provide an implantable cardiac stimulation system that is simpler to implant than prior art systems.

It is a further object of this invention to provide an implantable cardiac stimulation system that can be used with previously implanted defibrillation leads.

It is yet a further object of this invention to provide an implantable cardiac stimulation system that is safer to manufacture and Safer to implant.

It is yet a further object of this invention to provide a means to allow the implanting physician to make the defibrillator case either positive or negative for defibrillation.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

The invention will now be discussed in connection with the alternative choices it allows a surgeon to make at the time of implant of an implantable defibrillator. The decision to use either the pulse generator case as an electrode or to implant an additional lead, that is, whether the pulse generator can is electrically active or passive, is made by the implanting physician at the time of implant. The following are three examples of the many possible sequences of events in the decision making process:

EXAMPLE 1 a.) The defibrillator housing is activated for use as a subcutaneous (SQ)+ electrode in a midaxillary position, with RV–. The DFT is acceptable.

EXAMPLE 2 a.) The DFT is found to be too high using only two endocardial electrodes, with an RV electrode negative (–) and an SVC electrode positive (+).

b.) Various attempts are made to lower the DFT, such as repositioning the SVC electrode, reversing polarity, and changing pulse width. The DFT is still too high.

c.) A subcutaneous (SQ) electrode is desired for location on the left chest wall. However, it is determined that the patient is too thin in the pectoral region for the defibrillator generator to be implanted there, and thus its housing cannot be used as an electrode.

d.) A separate SQ electrode is implanted in the desired location. The DFT is found to be acceptable using RV–, SVC+, and SQ+.

e.) The inactive pulse generator is implanted in the abdominal region.

EXAMPLE 3 a.) The DFT is found to be too high using RV– and SVC+.

b.) The pulse generator housing is used as a SQ+ electrode in a midaxillary position, with RV– and SVC+. The DFT is still too high.

c.) Attempts are made to lower the DFT by repositioning the SQ pulse generator housing, such as by moving it more anterior or posterior. The DFT is still too high.

d.) The polarity is changed to make RV+, SVC–, and SQ–. The DFT is acceptable.

Figure 1:
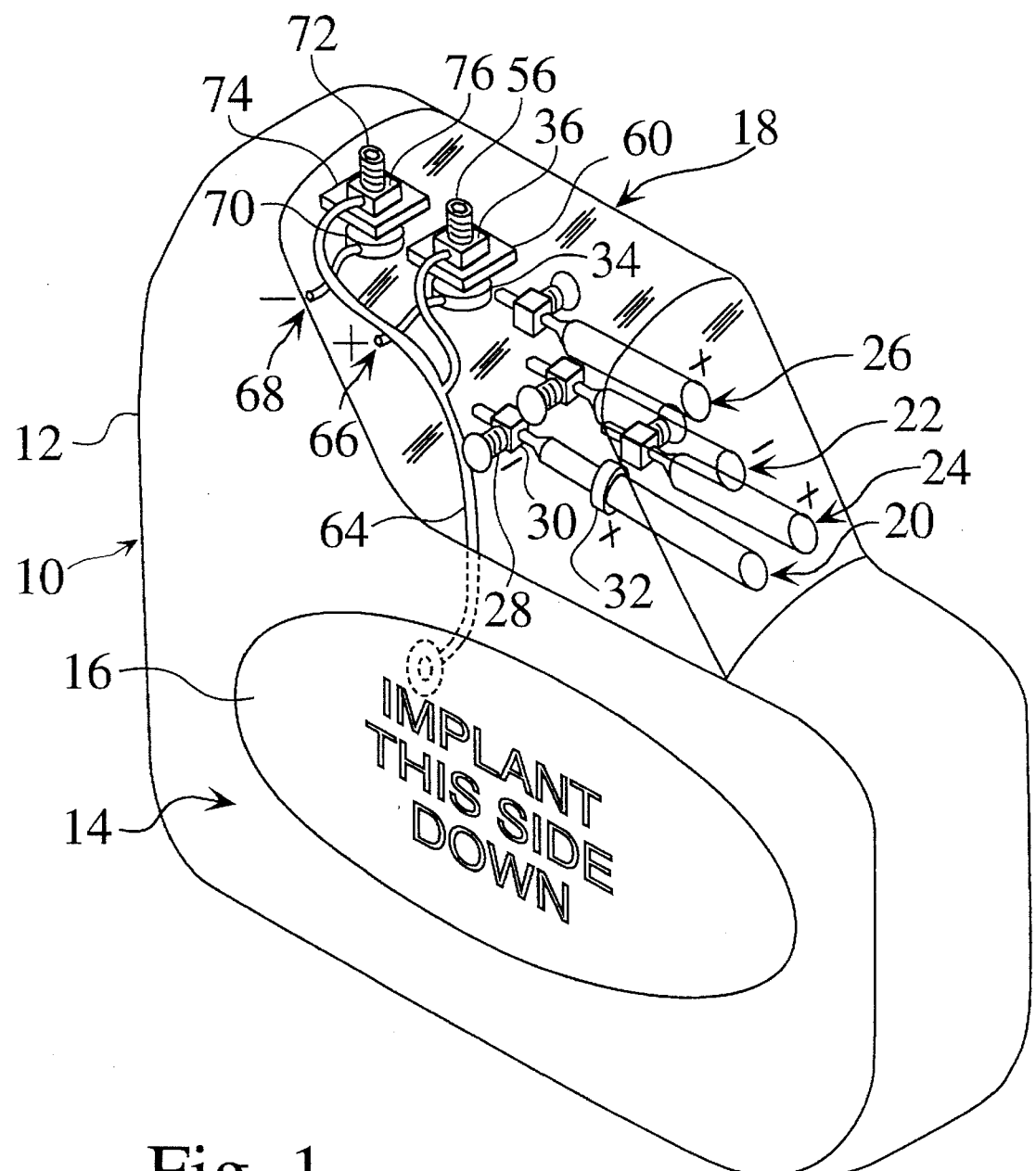
FIG. 1 illustrates the implantable defibrillator according to the present invention.

FIG. 1 illustrates an implantable pulse generator 10 according to the present invention. The defibrillator may have bradycardia and antitachycardia pacing capabilities as well as cardioversion and defibrillation capabilities. The housing 12 of the pulse generator 10 is typically titanium, although other corrosion resistant metals may be used. It may be partially insulated by a polymeric coating 14, and has an exposed, conductive portion 16 which may serve as an electrode. The polymeric insulating coating 14 serves to keep current flow between electrodes focused toward the heart during a defibrillation shock, so as to lower defibrillation thresholds and to avoid unwanted skeletal muscle stimulation. Alternatively, the entire housing outer surface may be left uncoated, and therefore conductive. The outer surface of the pulse generator may be of a special configuration to facilitate its discharge capabilities. Alternative means for insulating the can may be used, such as an insulative biocompatible boot having a cutout.

A header 18, which is preferably made of transparent or translucent polymeric material, such as epoxy, polyurethane, or silicone rubber, contains four lead connector cavities 20, 22, 24, and 26. Alternatively, the header 18 may be built into the housing 12, or may be made of an opaque material; however, this is not preferred since the cavities would not be visible. The connector cavities shown are a bipolar pacing lead connector cavity 20, and three unipolar defibrillator connector cavities 22, 24 and 26.

The pacing lead connector cavity 20 has setscrew threads 28 to a connector block 30 for making a mechanical and electrical connection to a pacing lead connector pin, and a garter spring 32 for making an electrical connection to a pacing lead connector ring. Alternatively, other connector mechanisms may be used to electrically and mechanically connect the pin and ring to the pulse generator, such as a setscrew connection instead of the garter spring. The pacing pin electrical connection 30 may be negative in polarity as shown, with the ring connection 32 positive. The pacing lead connector cavity 20 may be of the IS-1 BI type described in ISO 5841-3:1992(E) "Cardiac pacemakers—Part 3: Low-profile connectors (IS-1) for implantable pacemakers" (International Standard). Alternatively, the header may include a pair of pacing lead connector cavities for use with two lead connectors of a bipolar bifurcated lead, or other configurations, as are well known in the art.

The defibrillation lead connector cavities 22 and 24 are of opposite polarity, and are designed for high energy defibrillation pulses. The defibrillation connector cavity 26 is the same polarity as either cavity 22 or 24. Cavities 22, 24 and 26 may be of the DF-1 type described in ISO 11318:1993(E) "Cardiac defibrillators—Connector assembly for implantable defibrillators—Dimensional and test requirements" (International Standard), which accepts a "DF-1" connector pin of about 5 mm in length. Again, block and setscrew connections are shown, but any suitable connection mechanism known in the art may be used for the connector cavity conductive element, which interfaces with the lead connector pin to form the current-carrying connector contact. In use, the defibrillation lead connector cavities 22, 24, and 26 may have defibrillation leads inserted, or one or two of the cavities may have a plug inserted. Because the plug is used only to keep fluids out of the cavity, the plug may have a conductive or nonconductive pin.

Figure 4:
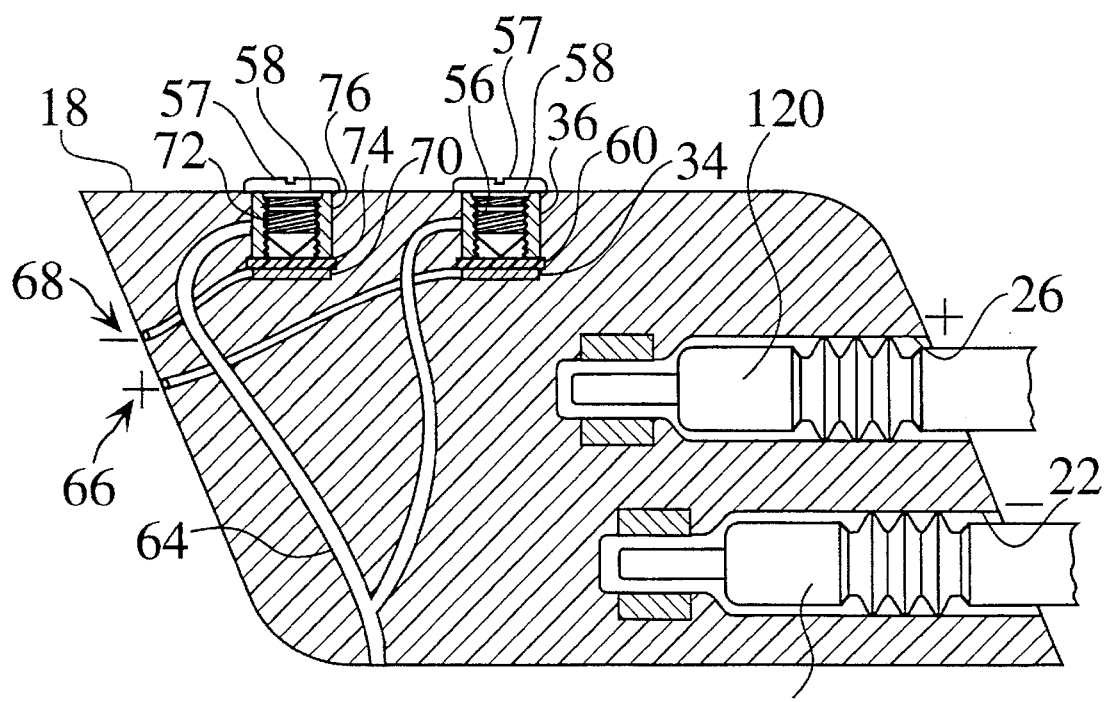
FIG. 4 is a cut away view showing a header having two case-activating setscrew blocks.
Figure 5:
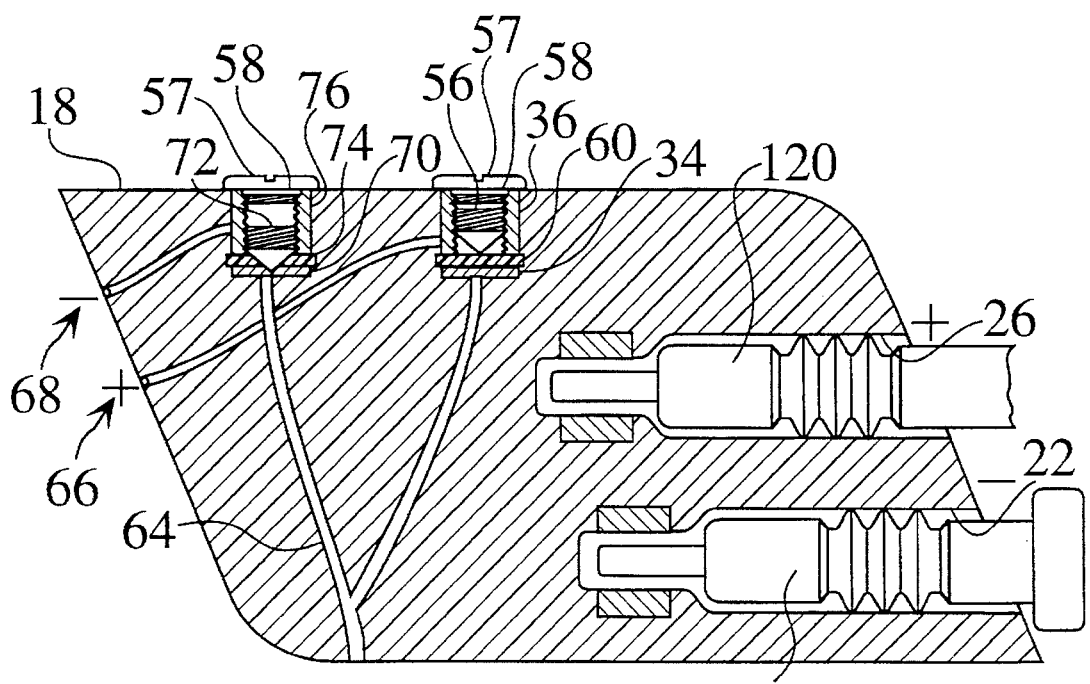
FIG. 5 is a cut away view showing a header having two case-activating setscrew blocks, and having the can activated with a negative polarity.

The defibrillator is provided with a contact 34 which is coupled to a positive terminal 66 of the defibrillator generator circuitry, and a contact 70 which is coupled to a negative terminal 68 of the defibrillator generator circuitry. Conductive elements 36 and 76, shown here as setscrew blocks, are electrically coupled to the conductive portion 16 of the defibrillator case 12 by conductor 64. Tightening a setscrew 56 in conductive element 36 will activate the pulse generator case 12 making it positive during a defibrillation shock. Tightening a setscrew 72 in conductive element 76 will make the pulse generator case negative during a defibrillation shock. Other electrical connection mechanisms could alternatively be used for the conductive elements 36 and 76 and setscrews 56 and 72 to interface with the contacts 34 and 70 to activate the case 12. As shown in FIGS. 4 and 5, all setscrews may be sealed with cap screws, medical adhesive, or the like.

By using the system of the present invention, various electrode configurations can be used as required to provide the optimum system for a given patient without having to bring two defibrillators into the operating room, one active and one inactive, and without requiring any programmability from the manufacturer or programming by the physician.

Another advantage provided by the defibrillator of the present invention is realized both during manufacture and during handling by implanting medical personnel. In a system having a permanently active can, or one that can be conventionally programmed to be active or inactive, there is the danger that the defibrillator could deliver a high voltage shock to anyone handling the device during manufacture or implant, because it is impossible to tell by visual inspection whether such a system is turned on, thus requiring interrogation using a programmer or similar method. On the other hand, the defibrillator case of the present invention is not active unless a setscrew tightened onto the appropriate contact, as can be easily noted by visual inspection. Simply by not tightening this setscrew, the defibrillator case remains inactive throughout the manufacturing process. During implant, the setscrew need not be tightened until near the end of the implant procedure. Once the setscrew is tightened, the defibrillator should be handled accordingly.

Other options for connector cavity configuration within the header are possible. For example, the header may be made smaller by providing only two defibrillator connector cavities instead of three.

Figure 2:
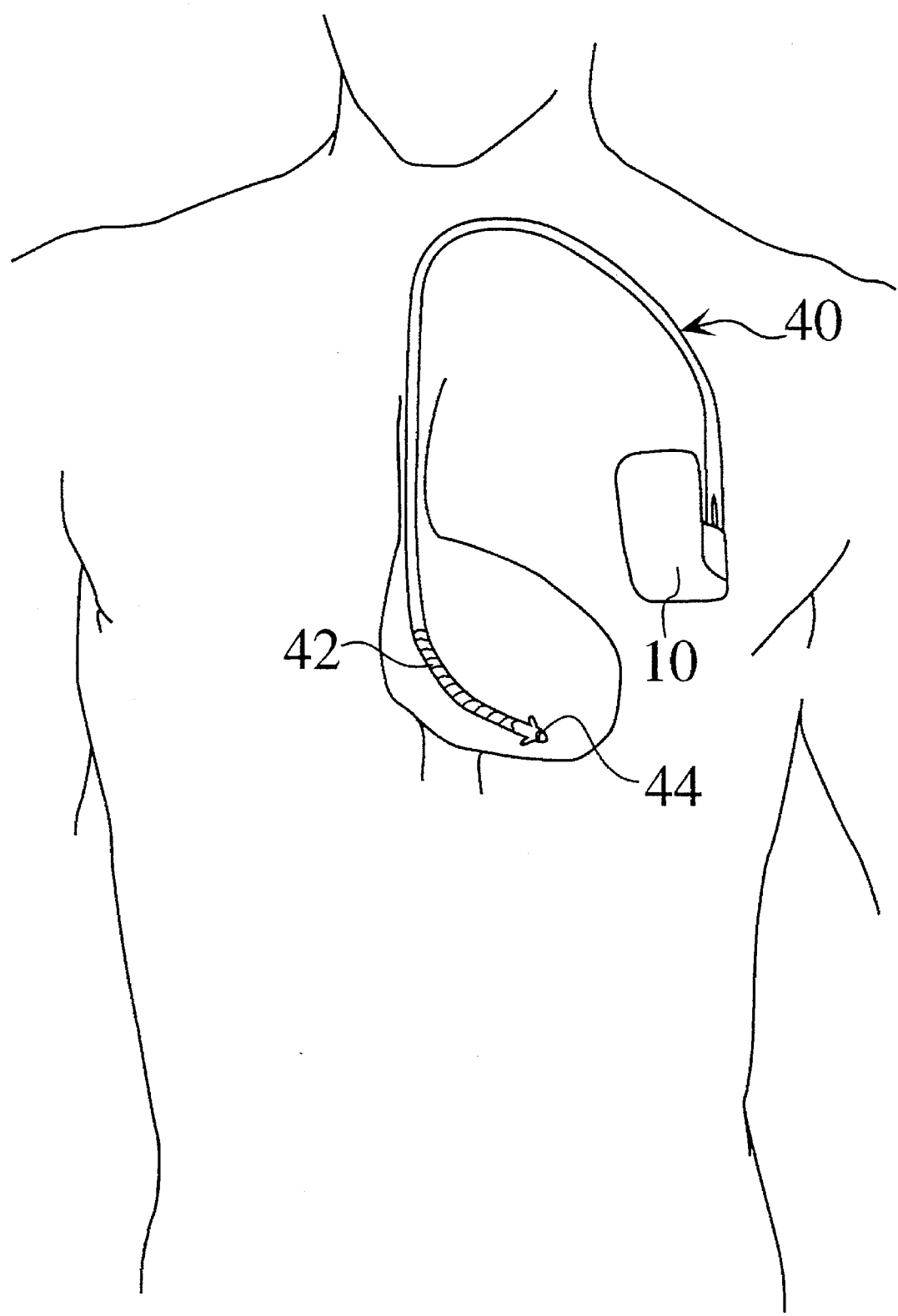
FIG. 2 illustrates the placement of an activated pulse generator case of the present invention in the patient's pectoral region adjacent the heart, connected to an implanted transvenous lead.

FIG. 2 illustrates the placement of the pulse generator 10 near the heart in the pectoral region of the patient. It is connected to an implanted transvenous lead 40, which has a pacing tip electrode 44 and one high surface area electrode 42 which is used alternately for defibrillation and for sensing. The electrodes are located in the right ventricle and the pulse generator 10 is located in the left pectoral region of the chest. Alternatively, the generator may be located at the level of the ventricles or in the abdominal region. The positive defibrillation lead connector cavity is plugged to prevent body fluids from entering it, using a plug similar to the one shown in FIG. 5. Alternatively, an electrode may be connected to this connector cavity.

It should also be noted that a defibrillator of the present invention may be used with preexisting leads. For example, if during a typical defibrillator replacement, due to end of battery life, the DFT is found to have increased in a patient having only RV and SVC electrodes, a replacement defibrillator of the present invention with an active can as an additional electrode may be used with the existing leads to decrease the DFT.

Figure 3:
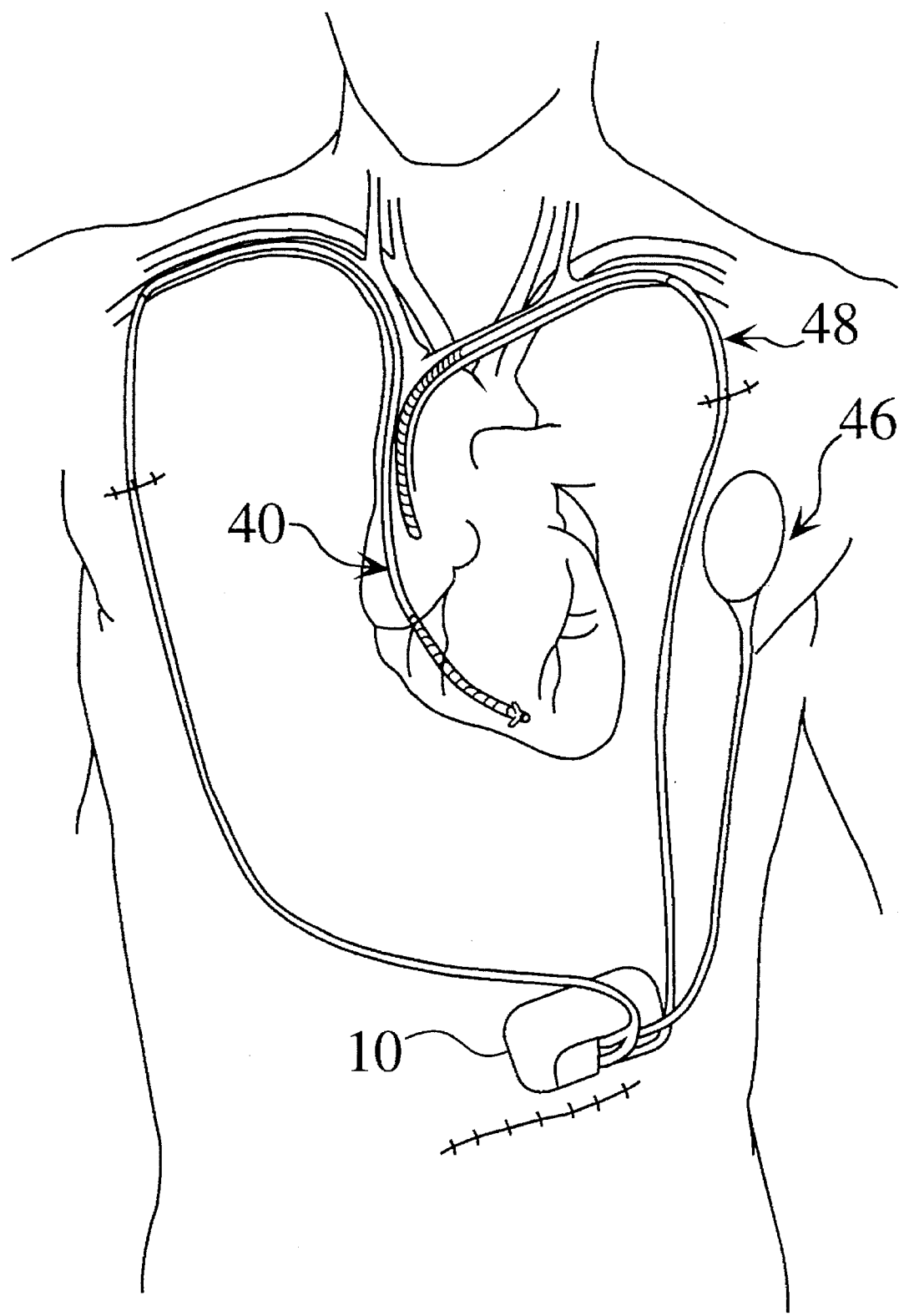
FIG. 3 illustrates the placement of an inactive pulse generator case of the present invention in the abdominal region, having a subcutaneous lead, a right ventricular lead, and a superior vend cava lead.

FIG. 3 illustrates the placement of a pulse generator 10 with an inactive case in the abdominal region, having a subcutaneous lead 46 implanted in the left chest wall, a right ventricular lead 40, and a superior vena cava lead 48.

FIG. 4 shows one embodiment of the invention, having first and second contacts, 34 and 70, respectively, first and second setscrews, 56 and 72, respectively, first and second insulative separators 60 and 74, and first and second conductive elements, 36 and 76, respectively. Conductive elements 36 and 76 are electrically coupled to the conductive portion of the defibrillator case by conductor 64. First contact 34 is electrically coupled to the positive high voltage terminal 66 of the pulse generator circuitry. Second contact 70 is electrically coupled to the negative high voltage terminal 68 of the pulse generator circuitry. High voltage terminals 66 and 68 are coupled to the positive and negative high voltage outputs of the pulse generator circuitry within housing 12 by hermetic feedthroughs (not shown). Tightening setscrew 56 onto contact 34, piercing insulative separator 60, makes the conductive portion of the defibrillator case 12 positive for defibrillation. Tightening setscrew 72 onto contact 70, piercing insulative separator 74, makes conductive portion 16 negative for defibrillation. Cavities 22 and 26 are shown with defibrillation leads 120 inserted. Cap screws 57 having o-rings 58 may be used to seal the setscrews and connector blocks and keep them electrically isolated from the body.

Note that insulative separator 60 is shown as an elastomeric membrane which may be easily pierced by setscrew 56. Alternatively, the seal may be a viscous, nonconductive silicone grease, silicone gel, or the like. The grease or gel is displaced by a setscrew, but then reforms to block the conductive fluid path between the contact 34 and conductive element 36 thereby achieving a fluid insulated connection. As another alternative, the seal may comprise an elastomeric membrane used in combination with a viscous, nonconductive grease.

FIG. 5 shows another embodiment of a defibrillator having two case-activating setscrew blocks, and having the can activated with a negative polarity. Defibrillator 10 has first and second contacts, 34 and 70, respectively, first and second setscrews, 56 and 72, respectively, first and second insulative separators 60 and 74, and first and second conductive elements, 36 and 76, respectively. Conductive element 36 is electrically coupled to the positive high voltage terminal 66 of the pulse generator circuitry. Conductive element 76 is electrically coupled to the negative high voltage terminal 68 of the pulse generator circuitry. Tightening setscrew 56 onto contact 34, piercing insulative separator 60, makes conductive portion 16 of the defibrillator case 12 positive for defibrillation. Tightening setscrew 72 onto contact 70, piercing insulative separator 74, makes the conductive portion of the pulse generator housing negative for defibrillation. Cap screws 57 having o-rings 58 are used to seal the setscrews and connector blocks and keep them electrically isolated from the body. Cavity 26 is shown having a defibrillation lead 120 inserted, and cavity 22 is shown with a plug 38 inserted to prevent body fluids from entering the cavity, keeping the cavity open for optional future use.

Figure 6:
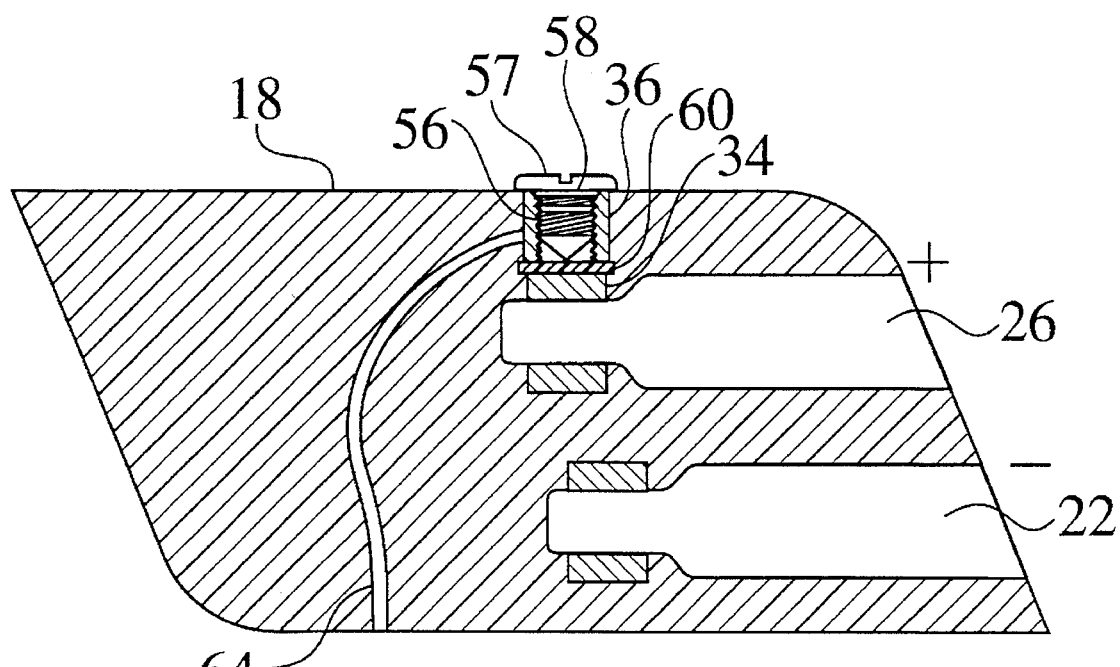
FIG. 6 is a cut away view showing another embodiment of a case-activating setscrew block.

FIG. 6 shows another embodiment of a case-activating setscrew block. In this embodiment, the connector block of defibrillation connector cavity 26 is used as contact 34. Because the connector block of cavity 26 is positive for defibrillation, and conductive element 36 is electrically coupled to the conductive portion of the defibrillator case via conductor 64, by piercing insulative separator 60 with setscrew 56 and tightening it down onto connector block contact 34, the conductive portion becomes positive for defibrillation. It should be noted that the connector block of defibrillation connector cavity 22 is also supplied with a case-activating setscrew block, although not shown, to provide the choice of making the defibrillator case positive or negative. A cap screw 57 having an o-ring 58 is used to seal each connector block and keep it electrically isolated from the body.

Figure 7:
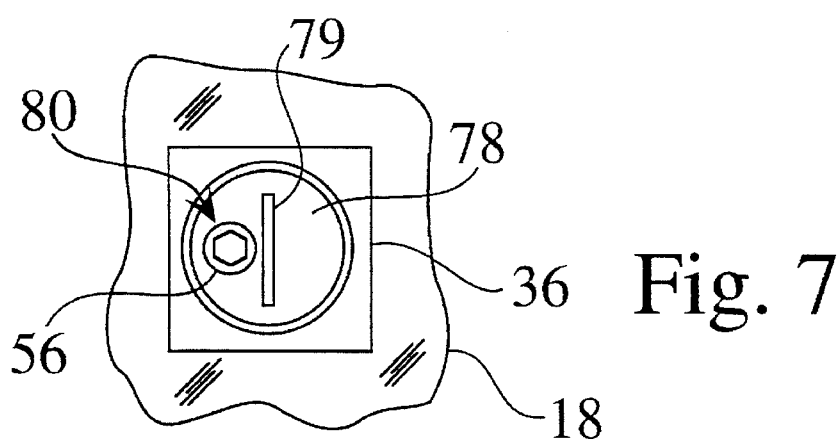
FIGS. 7 and 8 are top and side cut-away views of another embodiment of the case-activating setscrew of the present invention.
Figure 8:
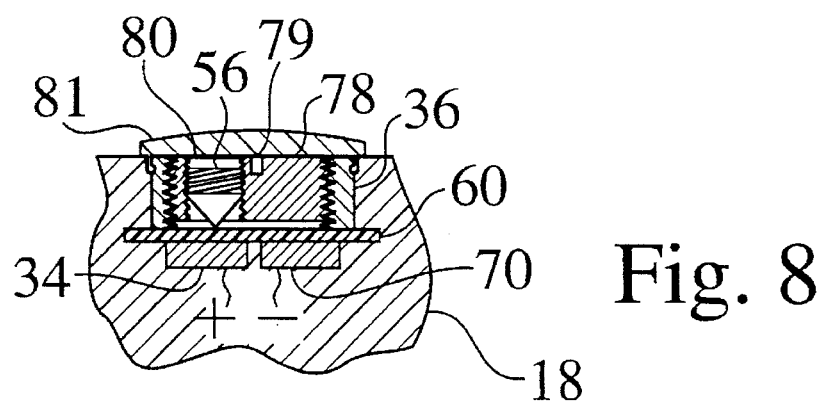

FIGS. 7 and 8 are top and side views, respectively, of an alternative embodiment of the invention. Conductive slotted screw 78 is positioned within a conductive block 36, and has a setscrew bore 80 through it on one side of a slot 79. The slotted screw 78 is positioned above positive and negative contacts, 34 and 70 respectively, which are isolated from the screw 78 by an insulative separator 60, which may also separate contacts 34 and 70 from each other. Alternatively, contacts 34 and 70 may be separated from each other by the material of the header 18 itself. Also, instead of using a single insulative separator 60, separate insulators may be used to isolate screw 78 from contact 34 and screw 78 from contact 70. Slotted screw 78 may be rotated to position setscrew bore 80 containing setscrew 56 directly above either positive contact 34 or negative contact 70. Tightening setscrew 56 will pierce separator 60 and make electrical contact with the contact 34 or 70 below. A sealing cap 81, shown only in FIG. 8, is used to isolate the entire conductive screw 78 from the body. An advantage of this embodiment is that it is not possible to accidentally make electrical contact to both contacts 34 and 70, which would short out the defibrillator.

Figure 9:
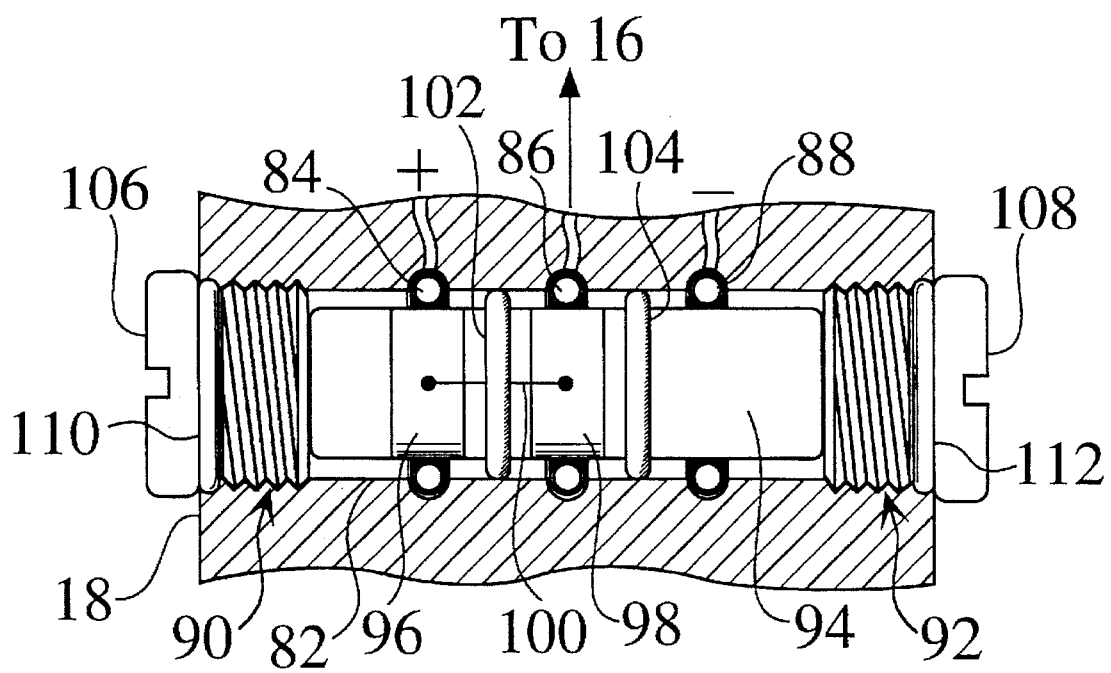
FIG. 9 is a cut-away view of yet another embodiment of the invention.

FIG. 9 is another embodiment of the invention which prevents accidental shunting between positive and negative terminals. Through hole 82 is formed in header 18, and comprises two threaded end portions 90 and 92 and three garter springs, 84, 86, and 88. Garter spring 84 is electrically connected to the positive high voltage terminal, garter spring 86 is electrically connected to the conductive portion 16 of pulse generator housing 12, and garter spring 88 is electrically connected to the negative high voltage terminal. An insert 94 has two conductive rings 96 and 98 that are electrically coupled to each other via conductor 100. Conductive ring 98 is located midway between the ends of insert 94. Sealing rings 102 and 104 are shown located on insert 94 on either side of conductive ring 98. Note that sealing ring 102 on insert 94 does not electrically separate conductive ring 96 from 98 since they are connected via conductor 100, but adds another barrier from one direction to keep garter spring 88 isolated from body fluid intrusion. Alternatively, the sealing rings may be located inside through hole 82 between garter springs 84 and 86 and between garter springs 86 and 88, instead of on insert 94. When insert 94 is inserted into through hole 82 oriented in the direction shown, garter springs 84 and 86 contact conductive rings 96 and 98 respectively, shorting the conductive portion 16 of pulse generator 12 to the positive high voltage terminal. Cap screws 106 and 108 are provided with o-rings 110 and 112 respectively, to seal through hole 84 from body fluids. When insert 94 is inserted in the reverse direction, the conductive portion 16 of the pulse generator 12 is made negative for defibrillation. To leave the can inactive, insert 94 is not used, and the ends of through hole 82 are simply sealed with end caps 106 and 108. It should also be noted that one end of insert 94 may have a sealing cap permanently built onto it, thus requiring only one cap screw to seal the opposite end of the through hole from body fluids. In that instance, the polarity of the case is determined by which side of the through hole 82 the insert 94 is entered. Alternatively, through hole 82 may be a blind hole, wherein the end of insert 94 first entering the hole 82 during installation determines the polarity of the active case. When using a blind hole, only one cap screw is needed to seal against body fluids.

Figure 10:
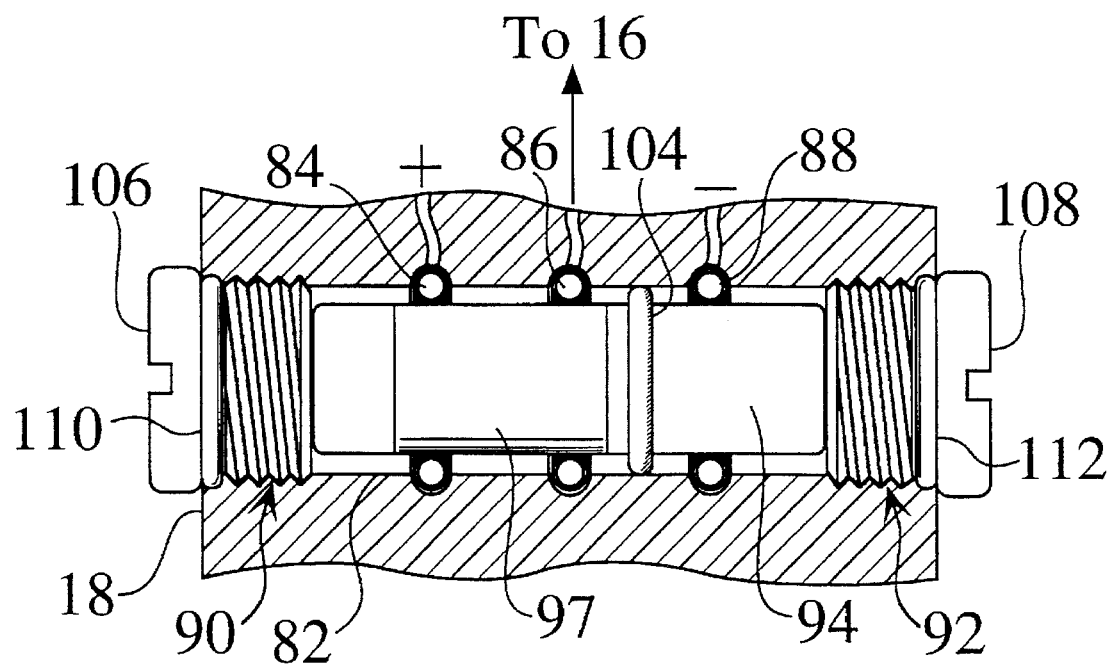
FIG. 10 is a cut-away view of another embodiment of the invention.
Figure 11:
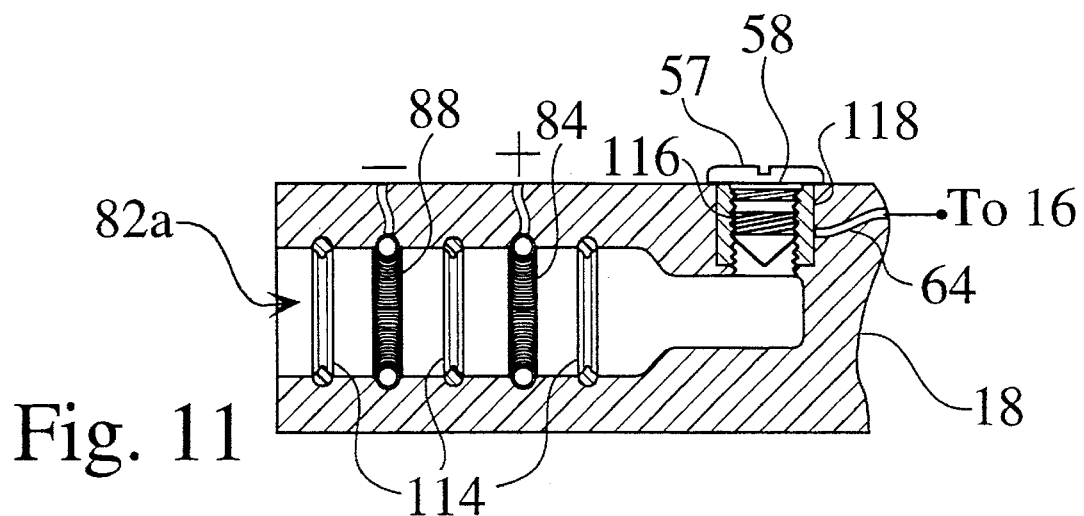
FIGS. 11–15 show another embodiment of the present invention having various plugs to activate the pulse generator case.
Figure 12:
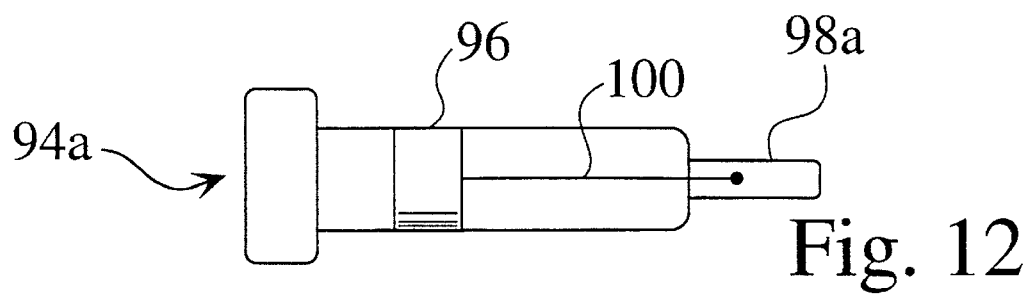
Figure 13:
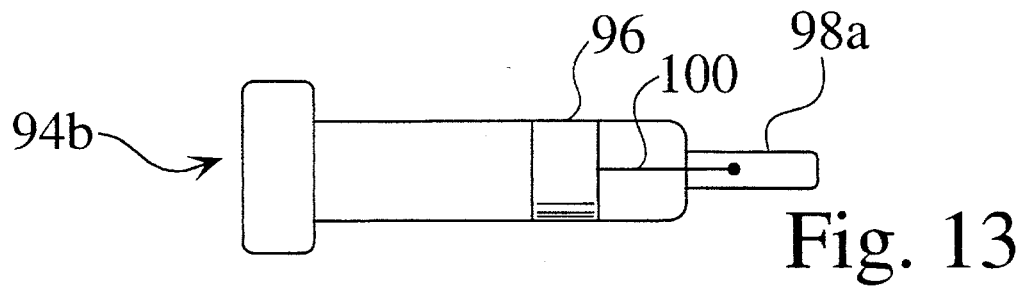

FIG. 10 shows an embodiment of the invention that is similar to that of FIG. 9, except that rings 96 and 98 and conductor 100 have been replaced by a larger conductive ring 97. Ring 97 is positioned on insert 94, covering generally the same positions as rings 96 and 98, such that it serves the same function.

Figure 14:
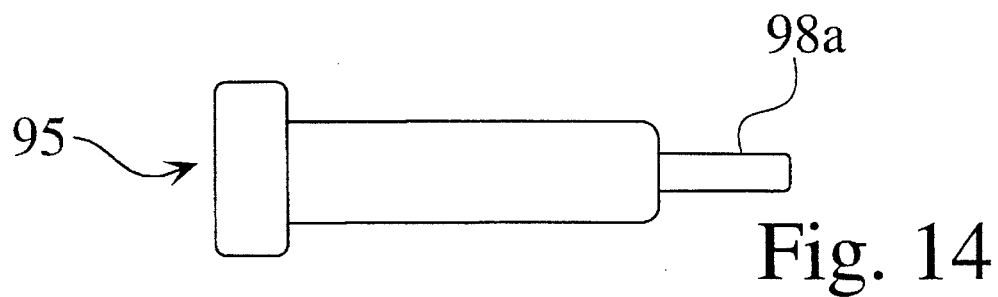
Figure 15:
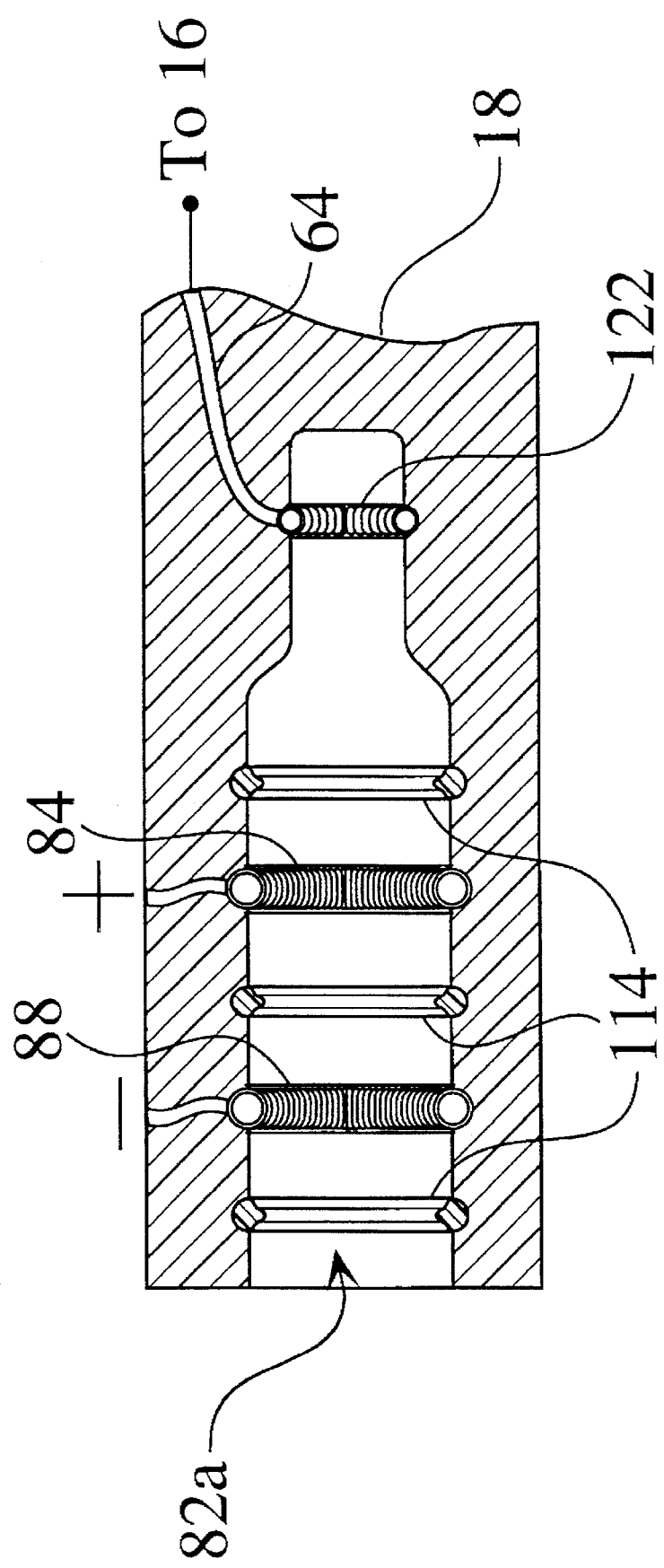

FIGS. 11–15 show yet another embodiment of the invention which allows the pulse generator case to be positive, negative, or electrically inactive, while preventing accidental current shunting between the positive and negative high voltage terminals. Header 18 is provided with a cavity 82a which has garter spring 88 coupled to the negative high voltage terminal and garter spring 84 coupled to the positive high voltage terminal. Setscrew 116 and connector block 118 are electrically coupled via conductor 64 to the conductive portion of the defibrillator case. Plug 94a has a ring 96 electrically coupled to pin 978a via conductor 100. When plug 94a is inserted and setscrew 116 is tightened down onto pin 978a, conductive ring 96 is in position to contact negative garter spring 88, and the case becomes negative for defibrillation. Likewise, when plug 94b is inserted and setscrew 116 is tightened down onto pin 978a, conductive ring 96 is in position to contact positive garter spring 84, and the case becomes positive for defibrillation. A cap screw 57 having an o-ring 58 may be used to seal connector block 118 and keep it electrically isolated from the body. A sealing plug 95 may be inserted into cavity 82a to seal against body fluids while maintaining the inactive status of the pulse generator case. Sealing rings 114 are shown located in cavity 82a in locations to isolate the positive and negative garter springs and setscrew block from each other and from the body. Alternatively, or in addition, sealing rings may be located on plugs 94a, 94b, and 95 to accomplish the same goal. The means to electrically connect the can to the pin 978a is shown in FIG. 14 as a setscrew and block assembly; this may alternatively be a garter spring 122 as shown in FIG. 15, or other means known in the art. Likewise, the garter springs 84 and 88 may be replaced by other contact mechanisms.

It should be understood that for all embodiments of the invention, setscrews 56 and 72 may be provided already located in setscrew blocks 36 and 76, but not tightened. Alternatively, the setscrews may be provided separately, either in the defibrillator package or as an accessory, to be inserted during implant. In addition, various methods known in the art may be used to seal the setscrew cavity from fluid ingress, such as cap screws, reseatable membranes, or medical adhesive applied over the setscrew.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An implantable cardiac defibrillator kit comprising:

a pulse generator case having an electrically conductive portion;

defibrillation pulse generator circuitry housed in said case, said pulse generator circuitry having first and second high voltage terminals of first and second polarity;

a header attached to said case, said header including first and second cavities, a conductive block electrically coupled to at least a portion of said pulse generator case, a first garter spring located in said first cavity at a first distance from said conductive block and electrically coupled to said first high voltage terminal, a second garter spring located in said first cavity at a second distance from said conductive block and electrically coupled to said second high voltage terminal and a conductive block located in said second cavity in electrical communication with said pulse generator circuitry;

a defibrillation lead having a defibrillation lead connector pin for insertion in said second cavity;

a first device for insertion into said first cavity, said device including a pin electrically coupled to a conductive ring, said ring located approximately said first distance from said first device pin; and a second device for insertion into said first cavity, said device including a pin electrically coupled to a conductive ring, said ring located approximately said second distance from said second device pin, whereby insertion of said first device into said first cavity makes said pulse generator case conductive portion said first polarity for defibrillation and insertion of said second device into said first cavity makes said pulse generator case conductive portion said second polarity for defibrillation.

2. The implantable cardiac defibrillator kit of claim 1, wherein said conductive block includes a setscrew for contacting said pin of either said first device or said second device when inserted into said first cavity.

3. The implantable cardiac defibrillator kit of claim 1, wherein said conductive block includes a garter spring for contacting said pin of either said first device or said second device when inserted into said first cavity.

4. The implantable cardiac defibrillator kit of claim 1 and further including sealing rings located in said first cavity between said first and second garter springs and between said garter springs and said conductive block.

5. The implantable cardiac defibrillator kit of claim 1 and further including at least one sealing ring located on each of said first and said second device.

6. The implantable cardiac defibrillator kit of claim 1 wherein said pulse generator case is partially encapsulated by a polymeric insulating coating.

* * * * *